(12) United States Patent
Hoey et al.

(10) Patent No.: US 11,864,810 B2
(45) Date of Patent: *Jan. 9, 2024

(54) SYSTEMS AND METHODS FOR TREATING THE BLADDER WITH CONDENSABLE VAPOR

(71) Applicant: Boston Scientific Scimed, Inc., Maple Grove, MN (US)

(72) Inventors: Michael Hoey, Shoreview, MN (US); Maximillian D. Fiore, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/647,219

(22) Filed: Jan. 6, 2022

(65) Prior Publication Data

US 2022/0125499 A1 Apr. 28, 2022

Related U.S. Application Data

(63) Continuation of application No. 16/891,262, filed on Jun. 3, 2020, now Pat. No. 11,246,641, which is a
(Continued)

(51) Int. Cl.
*A61B 18/04* (2006.01)
*A61B 18/00* (2006.01)
*A61B 17/00* (2006.01)

(52) U.S. Cl.
CPC .... *A61B 18/04* (2013.01); *A61B 2017/00522* (2013.01); *A61B 2018/00273* (2013.01);
(Continued)

(58) Field of Classification Search
CPC ........... A61B 2018/00273; A61B 2018/00517; A61B 2018/00523; A61B 2018/048;
(Continued)

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| CN | 2061443 U | 9/1990 |
| CN | 2418844 Y | 2/2001 |

(Continued)

OTHER PUBLICATIONS

US 5,326,343 A, 07/1994, Rudie et al. (withdrawn)
(Continued)

*Primary Examiner* — Sean W Collins
(74) *Attorney, Agent, or Firm* — Bookoff McAndrews, PLLC (57) ABSTRACT

A vapor delivery system and method is provided that is adapted for ablating bladder tissue to treat overactive bladder (OAB). The vapor delivery system includes an anchor tip configured anchor the system in the bladder while condensable vapor is delivered to target tissue. In one method, the vapor delivery system is advanced transurethrally into the patient to access the target tissue of the bladder, which can include a surface sensor of the bladder responsible for creating an urge incontinence sensation. The vapor delivery system includes a vapor source that provides a high quality vapor for delivery to tissue.

18 Claims, 6 Drawing Sheets

Related U.S. Application Data continuation of application No. 15/154,536, filed on May 13, 2016, now Pat. No. 10,702,327.

(60) Provisional application No. 62/160,963, filed on May 13, 2015.

(52) U.S. Cl.
CPC ............... *A61B 2018/00279* (2013.01); *A61B 2018/00517* (2013.01); *A61B 2018/00523* (2013.01); *A61B 2018/00577* (2013.01); *A61B 2018/00708* (2013.01); *A61B 2018/00839* (2013.01); *A61B 2018/00982* (2013.01); *A61B 2018/048* (2013.01); *A61B 2218/002* (2013.01); *A61B 2218/005* (2013.01)

(58) Field of Classification Search
CPC .......... A61B 18/04; A61B 2018/00279; A61B 2018/00839; A61B 2218/005; A61B 2017/00522; A61B 2018/00708; A61B 2018/00577; A61B 2218/002
See application file for complete search history.

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,249,585 A | 10/1993 | Turner et al. |
| 5,300,099 A | 4/1994 | Rudie |
| 5,312,399 A | 5/1994 | Hakky et al. |
| 5,330,518 A | 7/1994 | Neilson et al. |
| 5,366,490 A | 11/1994 | Edwards et al. |
| 5,370,609 A | 12/1994 | Drasier et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Undquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,021 A | 1/1999 | Thome et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,461,296 B1 | 10/2002 | Desai |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |
| 6,638,275 B1 | 10/2003 | McGaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |

(56) References Cited

U.S. PATENT DOCUMENTS

| | | |
|---|---|---|
| 6,726,696 B1 | 4/2004 | Houser et al. |
| 6,736,810 B2 | 5/2004 | Hoey et al. |
| 6,740,108 B1 | 5/2004 | Just et al. |
| 6,730,079 B2 | 6/2004 | Lovewell |
| 6,760,616 B2 | 7/2004 | Hoey et al. |
| 6,780,178 B2 | 8/2004 | Palanker et al. |
| 6,827,718 B2 | 12/2004 | Hutchins et al. |
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,369,894 B2 | 2/2008 | Gerber |
| 7,340,300 B2 | 3/2008 | Christopherson et al. |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,470,957 B2 | 6/2013 | Hikosaka et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,801,702 B2 | 8/2014 | Hoey et al. |
| 8,900,223 B2 | 12/2014 | Shadduck |
| 9,198,708 B2 | 12/2015 | Hoey et al. |
| 9,345,507 B2 | 5/2016 | Hoey et al. |
| 10,702,327 B2 * | 7/2020 | Hoey .................... A61B 18/04 |
| 11,246,641 B2 * | 2/2022 | Hoey .................... A61B 18/04 |
| 2002/0111617 A1 | 8/2002 | Cosman et al. |
| 2002/0078956 A1 | 9/2002 | Sharpe et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0186468 A1 | 9/2004 | Edwards |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1* | 6/2011 | Hoey ............... A61M 25/0068 604/26 |
| 2011/0264176 A1 | 10/2011 | Jackson et al. |
| 2011/0319759 A1 | 12/2011 | Liu et al. |
| 2012/0259271 A1 | 10/2012 | Shadduck et al. |
| 2012/0265276 A1 | 10/2012 | Curley |
| 2012/0323167 A1 | 12/2012 | Hoey et al. |
| 2013/0006231 A1 | 1/2013 | Sharma et al. |
| 2013/0066308 A1 | 3/2013 | Landman |
| 2013/0072855 A1 | 3/2013 | Sherry et al. |
| 2013/0074847 A1 | 3/2013 | Hoey et al. |
| 2013/0172867 A1 | 7/2013 | Shadduck et al. |
| 2013/0261692 A1 | 10/2013 | Cardinal et al. |
| 2014/0039356 A1* | 2/2014 | Sachs ................ A61B 18/1815 607/101 |
| 2014/0200568 A1 | 7/2014 | Sharma |

(56) References Cited

U.S. PATENT DOCUMENTS

| | | |
|---|---|---|
| 2014/0276713 A1 | 9/2014 | Hoey et al. |
| 2014/0288543 A1 | 9/2014 | Hoey et al. |
| 2014/0354381 A1 | 12/2014 | Kohihafer |
| 2015/0025515 A1 | 1/2015 | Hoey et al. |
| 2015/0126990 A1 | 5/2015 | Sharma et al. |
| 2015/0157384 A1 | 6/2015 | Hoey et al. |
| 2015/0157389 A1* | 6/2015 | Ben-Ezra ............... A61B 17/32 606/41 |
| 2016/0015445 A1 | 1/2016 | Hoey et al. |
| 2016/0081736 A1 | 3/2016 | Hoey et al. |
| 2017/0056089 A1 | 3/2017 | Hoey et al. |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101803947 A | 8/2010 |
| JP | 7-507696 A | 8/1995 |
| JP | 8-501957 A | 3/1996 |
| JP | 8-504613 A | 5/1996 |
| JP | 11-318925 A | 11/1999 |
| JP | 200014663 A | 1/2000 |
| JP | 2000005191 A | 1/2000 |
| JP | 2001500763 A | 1/2001 |
| JP | 2005137916 A | 6/2005 |
| WO | 92/10142 A1 | 6/1992 |
| WO | 01/24715 A1 | 4/2001 |
| WO | 03/088851 A1 | 10/2003 |
| WO | 03/0986871 A2 | 11/2003 |
| WO | 2006/004482 A1 | 1/2006 |
| WO | 2008/083407 A1 | 7/2008 |
| WO | 2010/080467 A2 | 7/2010 |
| WO | 2013/160772 A2 | 10/2013 |
| WO | 2017/106843 A1 | 6/2017 |

OTHER PUBLICATIONS

Hoey et al.; U.S. Appl. No. 15/851,333 entitled "Vapor ablation systems and methods," filed Dec. 21, 2017.

Hoey et al.; U.S. Appl. No. 15/864,957 entitled "Transperineal Vapor ablation systems and methods," filed Jan. 8, 2018.

Hoey et al.; U.S. Appl. No. 15/900,295 entitled "Systems and methods for prostate treatment," filed Feb. 20, 2018.

HAI; Photoseleclive Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4 ); Dwnld from http://www.prostate-cancer.org/pcricms/node/233 on May 10, 2012; 4 pages.

Nguyen et al; Updated results of magnetic resonance imaging guided partial prostate brachytherapy for favorable risk prostate cancer: implications for focal therapy; J. Ural.; 188(4 ); pp. 1151-1156; Oct. 2012.

Hastings et al.; U.S. Appl. No. 15/011,005 entitled "Vapor ablation systems and methods," filed Jan. 29, 2016.

Hastings et al.; U.S. Appl. No. 15/035,944 entitled "Vapor ablation systems and methods," filed May 11, 2016.

* cited by examiner

SYSTEMS AND METHODS FOR TREATING THE BLADDER WITH CONDENSABLE VAPOR

CROSS REFERENCE TO RELATED APPLICATIONS

This application is a continuation of U.S. application Ser. No. 16/891,262, filed Jun. 3, 2020, which is a continuation of U.S. application Ser. No. 15/154,536, filed May 13, 2016, now U.S. Pat. No. 10,702,327, issued Jul. 7, 2020, which claims the benefit of U.S. Provisional Patent Application No. 62/160,963, filed May 13, 2015, each of which is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to devices and related methods for treatment of bladder using a minimally invasive approach. More specifically, this disclosure relates to treating overactive bladder with condensable vapor.

BACKGROUND

Overactive Bladder (OAB) is a condition affecting millions of people. Symptoms include uncontrollable urges to urinate and incontinence. Frequent and sudden urges to urinate can negatively impact quality of life in those affected by the disorder.

Current treatment of OAB includes lifestyle changes including fluid restriction, avoidance of caffeine, and pelvic floor muscle exercise. Medications can also treat some symptoms of OAB but are only moderately effective. Surgical procedures have also been used including botox injections or electrical stimulation of the bladder, but the long-term effectiveness of these treatments is unknown.

It is postulated that OAB is caused by increased connectivity and excitability of both detrusor smooth muscle and nerves. Increased excitability and connectivity of nerves involved in micturition rely on growth factors that orchestrate neural plasticity. Neurotransmitters, prostaglandins, and growth factors, such as nerve growth factor, provide mechanisms for bidirectional communication between muscle or urothelium and nerve, leading to OAB with or without urge incontinence.

SUMMARY OF THE DISCLOSURE

A method for treating overactive bladder is provided, comprising the steps of inserting a vapor delivery system into a urethra of a patient, advancing a distal portion of the vapor delivery system to a bladder of the patient, viewing the distal portion of the vapor delivery system with a camera disposed on or within the vapor delivery system, deploying a vapor delivery tip from the vapor delivery system into the bladder tissue to deform the tissue without penetrating the tissue, and delivering vapor into the bladder tissue to damage nerves, smooth muscle urothelium and other excitable tissue in the bladder.

In some embodiments, the delivering step comprises delivering between 1 calorie of energy and 500 calories of energy into the bladder at multiple locations with the idea of necrosing excitable tissues for the purpose of reducing the symptoms of overactive bladder, painful bladder syndrome and/or interstitial cystitis.

A method for treating overactive bladder in a patient is provided, comprising the steps of inserting a vapor delivery catheter into a urethra of the patient, advancing a distal anchor tip of the vapor delivery catheter transurethrally into a bladder of the patient, positioning the distal anchor tip on or adjacent to a target tissue including a surface sensor of the bladder responsible for creating an urge incontinence sensation, advancing the distal anchor tip into the target tissue to deform the bladder without puncturing the bladder, and delivering vapor through the vapor delivery system to the target tissue to ablate the target tissue including the surface sensor.

In some embodiments, the method further comprises delivering between 1 and 500 calories of energy to the target tissue.

In other embodiments, the method further comprises advancing the distal anchor tip less than 10 mm into the target tissue.

In alternative embodiments, the method further comprises advancing the distal anchor tip less than 5 mm into the target tissue.

In one embodiment, the distal anchor tip cannot extend more than 5 mm into the target tissue.

In another embodiment, the distal anchor tip cannot extend more than 1-2 mm into the target tissue.

In some embodiments, the advancing step further comprises advancing a needle of the distal anchor tip into the target tissue.

In another embodiment, the delivering step further comprises delivering vapor through vapor delivery ports disposed on a distal catheter tip of the vapor delivery system.

In other embodiments, the delivering step further comprises delivering vapor through at least one vapor delivery port disposed on the distal anchor tip of the vapor delivery system.

In one embodiment, the vapor is delivered through the vapor delivery ports to create one or more concentric spray patterns configured to form concentric treatment rings in the target tissue.

In some embodiments, the method further comprises ablating the target tissue to a depth of 1-3 mm.

A vapor delivery system is also provided, comprising a handle portion, an elongate flexible shaft connected to the handle portion, the elongate flexible shaft including a distal anchor tip configured to anchor the elongate flexible shaft into a bladder of a patient without puncturing through the bladder, a vapor source, at least one vapor delivery port disposed on the elongate flexible shaft and fluidly coupled to the vapor source, and an electronic controller operatively coupled to the vapor source and configured to deliver vapor through the at least one vapor delivery port to ablate the bladder.

In some embodiments, the distal anchor tip comprises a conical shape.

In other embodiments, the distal anchor tip comprises a pyramid shape.

In alternative embodiments, the distal anchor tip comprises a needle tip.

In one embodiment, the needle tip is configured to be retracted into the flexible elongate shaft during insertion into a patient and is configured to be advanced out of the flexible elongate shaft prior to vapor delivery.

The In some embodiments, the at least one vapor delivery port is arranged to create one or more concentric spray patterns configured to form concentric treatment rings in the bladder.

In other embodiments, the distal anchor tip is steerable.

In some embodiments, the distal anchor tip cannot extend more than 10 mm into the bladder.

In additional embodiments, the distal anchor tip cannot extend more than 1-5 mm into the bladder.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION

In general, one method for treating overactive bladder comprises introducing a heated vapor into contact with excitable tissue near the surface of the urothelium in the bladder that create the urge incontinence sensation. The method can cause localized ablation of bladder tissue to minimize urge incontinence or overactive bladder (OAB), painful bladder syndrome (PBS) and/or interstitial cystitis. The present disclosure is directed to the treatment of OAB, and more particularly for transurethrally ablating excitable tissue structures in the bladder that are responsible for urge incontinence.

The system can include a vapor delivery mechanism that delivers vapor media, including water vapor. The system can utilize a vapor source configured to provide vapor having a temperature of at least 60-140° C. In another embodiment, the system further comprises a computer controller configured to deliver vapor for an interval ranging from 1 second to 30 seconds.

In some embodiments, the system further comprises a source of a pharmacologic agent or other chemical agent or compound for delivery with the vapor. These agents include, without limitation, an anesthetic, an antibiotic or a toxin such as Botox®, or a chemical agent that can treat cancerous tissue cells. The agent also can be a sealant, an adhesive, a glue, a superglue, an anti-inflammatory, an antibiotic, or the like.

Figure 1:
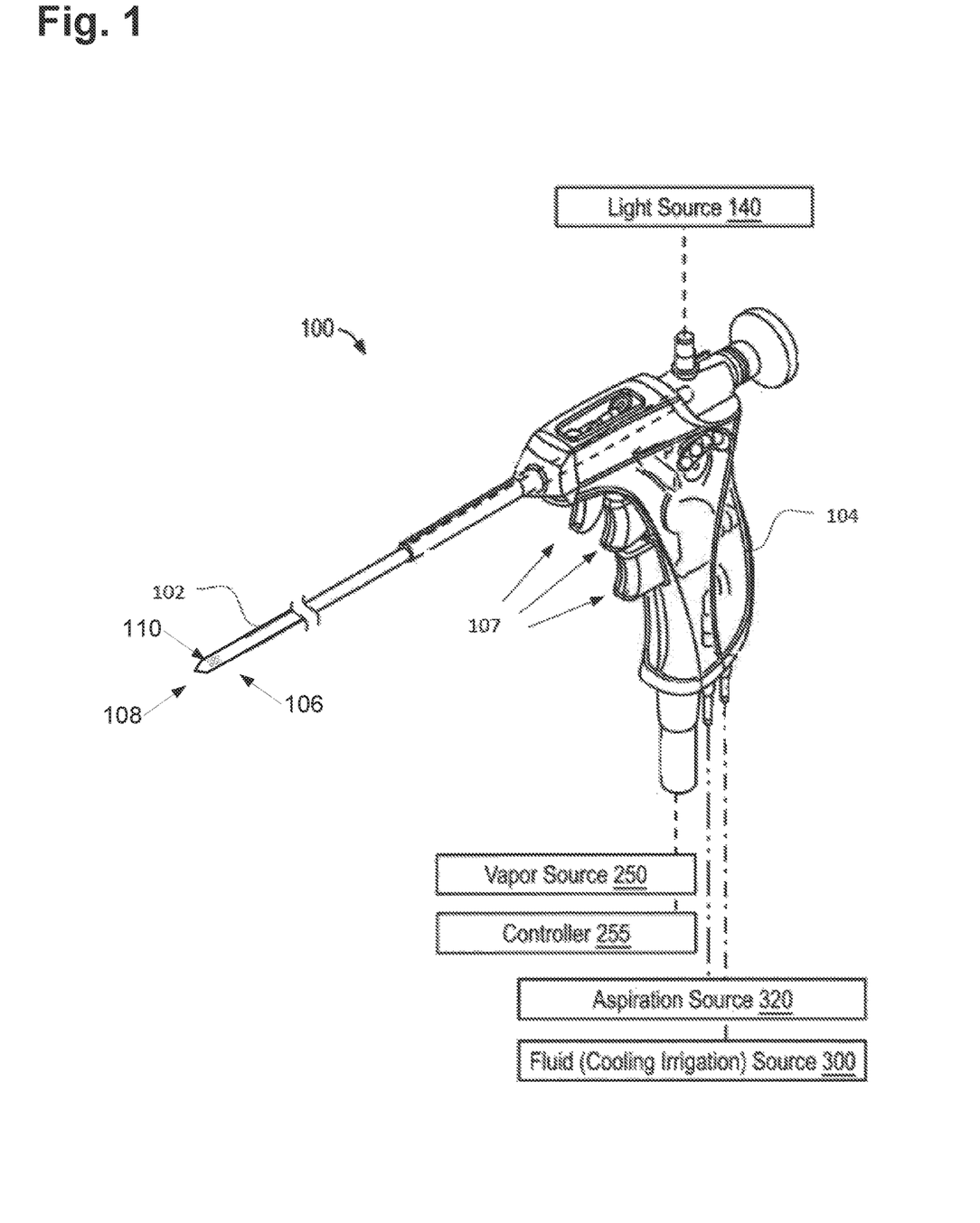
FIG. 1 shows one embodiment of a vapor delivery system.

FIG. 1 shows one embodiment of a vapor delivery system. Vapor delivery system 100 can have an elongate flexible shaft 102 configured for insertion into the urethra of a patient and a handle portion 104 for gripping with a human hand. The vapor system 100 can include a distal catheter tip 106 that includes an anchor tip 108 and one or more vapor delivery ports 110. In some embodiments, the distal catheter tip can be deformable and/or steerable.

The one or more vapor delivery ports 110 are fluidly coupled to the vapor source and can be configured to deliver a flow of vapor media from a vapor source 250 through the vapor elongate flexible shaft 102 into bladder tissue. The vapor delivery system can further include an aspiration source 320 configured to aspirate tissue and/or fluids from the patient (e.g., either through the vapor delivery ports or through separate aspiration ports in the distal catheter tip), and can also include a fluid source 300 configured to deliver a fluid or cooling irrigation to the tissue before, during, and/or after vapor delivery.

The vapor delivery system 100 of FIG. 1 can include a plurality of actuation devices 107, such as triggers, buttons, or levers, which can be configured to actuate the various functions of the system. For example, the actuation devices can be configured to steer the distal catheter tip, and start/stop the flow of vapor, aspiration, and/or the cooling irrigation.

Vapor source 250 is provided for generating and/or delivering a vapor media through the distal catheter tip to ablate or damage tissue. The vapor source can be a vapor generator that can deliver a vapor media, such as water vapor, that has a precisely controlled quality to provide a precise amount of thermal energy delivery, for example measured in calories per second. In some embodiments, the vapor source can comprise an inductive heating system in which a flow media is inductively heated to generate a condensable vapor. The vapor source can be external to the vapor delivery system, or alternatively, can be integrated into the handle and or elongate flexible shall of the vapor delivery system.

The controller 255 can be set to control the various parameters of vapor delivery, for example, the controller can be set to delivery vapor media for a selected treatment interval, a selected pressure, or selected vapor quality. Further details on the vapor delivery system, the vapor generator, and how vapor and fluid are delivered to tissue can be found in U.S. Pat. No. 8,273,079 and PCT Publication No. WO 2013/040209, both of which are incorporated by reference. In some embodiments, the electronic controller can also control the aspiration and/or cooling irrigation functions of the vapor delivery system.

As described above, the vapor delivery system can be connected to a vapor source 250, an aspiration source 320, a fluid or irrigation source 300, a light source 140, and an electronic controller 255 configured to control generation and delivery of vapor from the vapor source, through a lumen of the shaft, through the distal catheter tip, and into tissue. In some embodiments, the electronic controller can be disposed on or in the vapor delivery system, and in other embodiments the electronic controller can be disposed separate from the system.

Referring still to FIG. 1, the fluid or irrigation source 300 can provide a fluid, such as saline, through a separate lumen in the shaft to provide irrigation and flushing to tissue during insertion of the system and during vapor delivery to tissue. In some embodiments, the irrigation can be used to clear blood and debris from tissue lumens to increase visibility. The irrigation can also provide cooling to the urethra and/or bladder of the patient, both via direct contact of the irrigation fluid with the tissue as well as cooling the shaft of the vapor delivery system as the fluid flows from the irrigation source through the shaft and into contact with the tissue.

Figure 2:
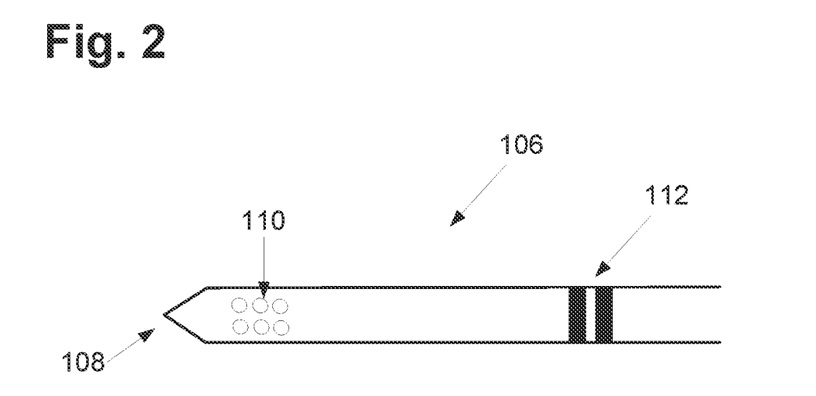
FIG. 2 shows a close-up view of a distal portion of the vapor delivery system.

FIG. 2 shows a close-up view of the distal catheter tip 106 of the vapor delivery system. The elongate shaft and the distal catheter tip are sized and configured to be inserted into a lumen of a flexible cystoscope. The distal catheter tip can further include a distal anchor tip 108 that is configured to be forced or anchored partially into tissue of the bladder to deform the tissue without penetrating the tissue. When the distal anchor tip 108 is deforms the bladder it can anchor the vapor delivery system in the target tissue of the bladder. In one embodiment, the pointed tip can be a conical or pyramid shaped pointed tip. In embodiments where the pointed tip is a pyramid shaped pointed tip, the pyramid shape can include two, three, or more faces. By deforming the tissue without penetrating the tissue, the pointed anchor tip can be anchored in the bladder tissue near the target nerves or sensors to be treated without compromising the structural integrity of the bladder.

When the pointed anchor tip is anchored in the bladder tissue, vapor can be delivered from the vapor source to the bladder tissue through the one or more vapor delivery ports 110. In some embodiments, the vapor ports can be disposed proximally to the anchor tip 108 on the shaft. In other embodiments, the vapor ports can also be disposed on the anchor tip itself.

The position of the vapor ports with respect to the anchor tip determines the vapor spray pattern, which can be adjusted and designed according to the desired thermal ablation in the tissue. In one embodiment, the vapor ports can be arranged in a concentric manner on the tip and/or shaft to create one or more concentric spray patterns configured to form concentric treatment rings in the bladder tissue. Vapor can be delivered to the bladder to ablate the tissue to a specific depth that damages the targeted bladder sensors without ablating the full thickness of the bladder tissue. For example, in some embodiments, the vapor can be delivered to the bladder tissue to ablate a depth of 1-6 mm of bladder tissue. It is desired to treat only a small depth of tissue to achieve the goal of damaging the sensors without ablating a whole through the entirety of the bladder tissue.

The distal catheter tip can optionally include visualization features 112, which can be markings on the catheter tip. The visualization features 112 can include, for example, stripes, shapes, colors, or other visual features disposed directly on the distal catheter tip. When the distal catheter tip is extended beyond the cystoscope during an ablation procedure, the visualization features can be viewed under visualization (e.g., with a camera) of the cystoscope during to determine when the distal catheter tip is advanced the proper distance beyond the cystoscope. Also, the markings on the catheter can be used to guide the clinician in placing the catheter in the proper orientation to deliver a vapor pattern in a prescribed pattern. For example, the visualization features can include a feature to indicate where the vapor delivery ports are oriented on the distal catheter tip, or the visualization features may be disposed on the shaft only in sections where vapor delivery ports are located.

The pointed anchor tip of the vapor delivery system prevents slippage and anchors the vapor delivery system when a clinician pushes the vapor delivery system into the bladder. As the clinician pushes harder, the vapor delivery system deforms the bladder as it continues to extend beyond the cystoscope. The clinician can determine the level of bladder deformation by observing the distance of the visualization features from the cystoscope. The amount of bladder deformation also determines the pattern of vapor deposition from the vapor delivery ports onto the bladder tissue. Vapor can be delivered from the vapor delivery system onto or into the bladder tissue when the appropriate pattern of vapor deposition is achieved.

Figure 3:
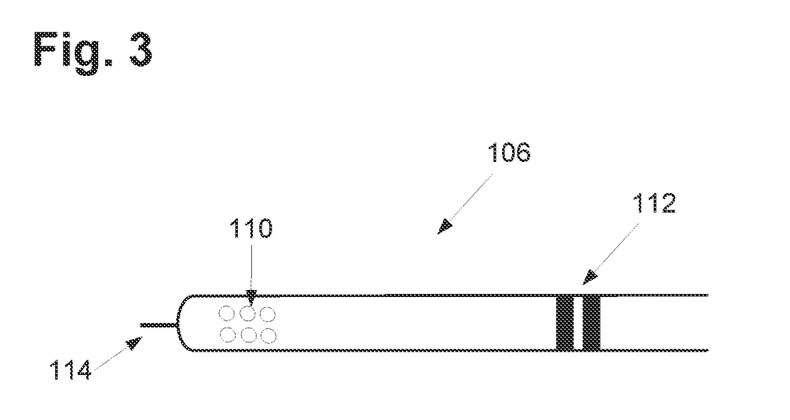
FIG. 3 shows another embodiment of a distal portion of the vapor delivery system.

FIG. 3 shows an alternate embodiment of a distal catheter tip 106, which includes a needle anchor tip 114 configured to be forced into the tissue of the bladder to deform the tissue without fully penetrating the tissue. The needle anchor tip 114 can operate in a similar manner to the pointed anchor tip described above. In some embodiments, the needle anchor tip 114 can include one or more vapor delivery ports disposed on or in the needle, or at the very distal tip of the needle.

In some embodiments, the needle anchor tip can be retracted into the distal catheter tip during navigation to the bladder, and advanced out of the catheter tip to anchor the system for vapor delivery. For example, an actuation device on the vapor delivery system can control advancement and retraction of the needle. In some embodiments, the needle can be designed to advance a limited distance from the distal tip of the catheter so as to not fully penetrate through or puncture bladder tissue. For example, bladder tissue can typically range from 5-15 mm in thickness. In some embodiments, the needle anchor tip 114 cannot extend more than 10 mm into the tissue so as to not puncture through the bladder tissue. In some embodiments, the clinician can determine the thickness of the patient's bladder (such as with visualization) and adjust the length of the needle anchor tip to be less than the thickness of the bladder. In other embodiments, the needle anchor tip cannot extend more than 1-5 mm into the tissue, which can be sufficient to anchor the catheter tip in the bladder tissue but not be long enough to puncture the bladder tissue in the vast majority of potential patients. Once the system is anchored in the tissue with the needle anchor tip, vapor can be delivered to the bladder tissue through vapor delivery ports 110.

Figure 4:
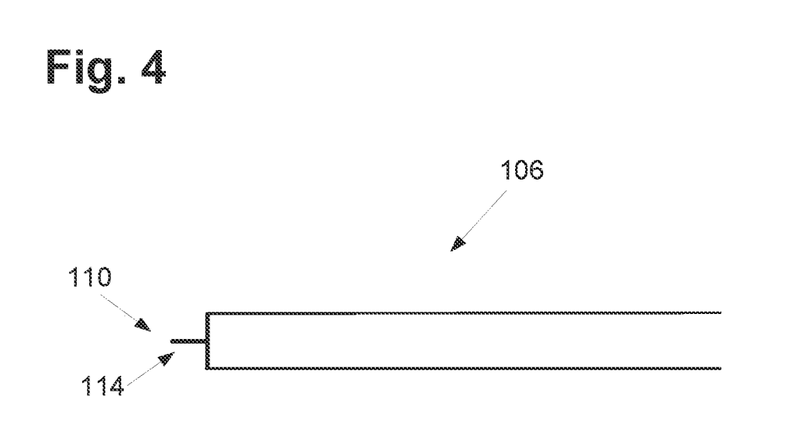
FIG. 4 shows yet another embodiment of a distal portion of the vapor delivery system.

FIG. 4 shows another embodiment of a distal catheter tip 106 having a needle anchor tip 114, similar to the embodiment described above in FIG. 3. However in this embodiment, the vapor delivery port(s) 110 are located on or in the needle anchor tip 114 itself, instead of being located on the catheter shaft. The vapor delivery port(s) 110 can be located at the distal end of the needle anchor tip 114, for example. This configuration allows for the needle anchor tip 114 to anchor the distal catheter tip in tissue, and to deliver vapor through the vapor delivery ports 110 directly into the bladder tissue.

Figures 5A, 5B:
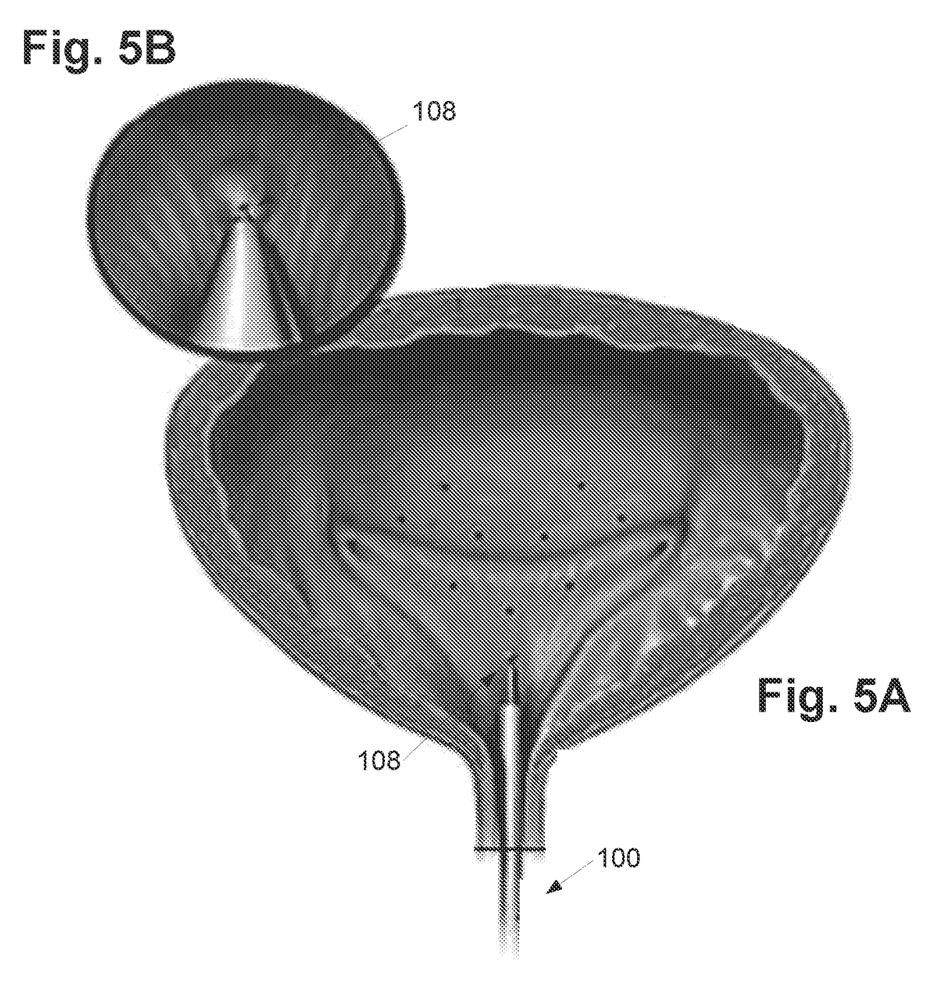
FIGS. 5A-5B illustrate one method of treatment using the vapor delivery system.

Referring to FIG. 5, the device and method of this disclosure provide a precise, controlled thermal ablative treatment of tissue in the bladder for the treatment of OAB. In particular, the ablative treatment is configured to ablate surface sensors in or near the bladder that create the urge incontinence sensation to treat OAB.

Sensory perception of the urge to urinate may be mediated by two bladder sensors. The first sensor, located at the trigone and posterior urethra, is sensitive to small changes in pressure and may function as an early warning system of bladder filling. Some instances of urge incontinence result when the early warning system fails and detrusor contraction occurs just shortly after the second sensor is stimulated. Thus, two forms of urge incontinence may be associated with loss of the first sensor: one with and the other without associated frequency, with the difference being the presence or absence of detrusor instability. The method described herein describes a technique for ablating sensors with vapor to achieve a permanent effect to minimize urge incontinence or OAB.

Figure 6:
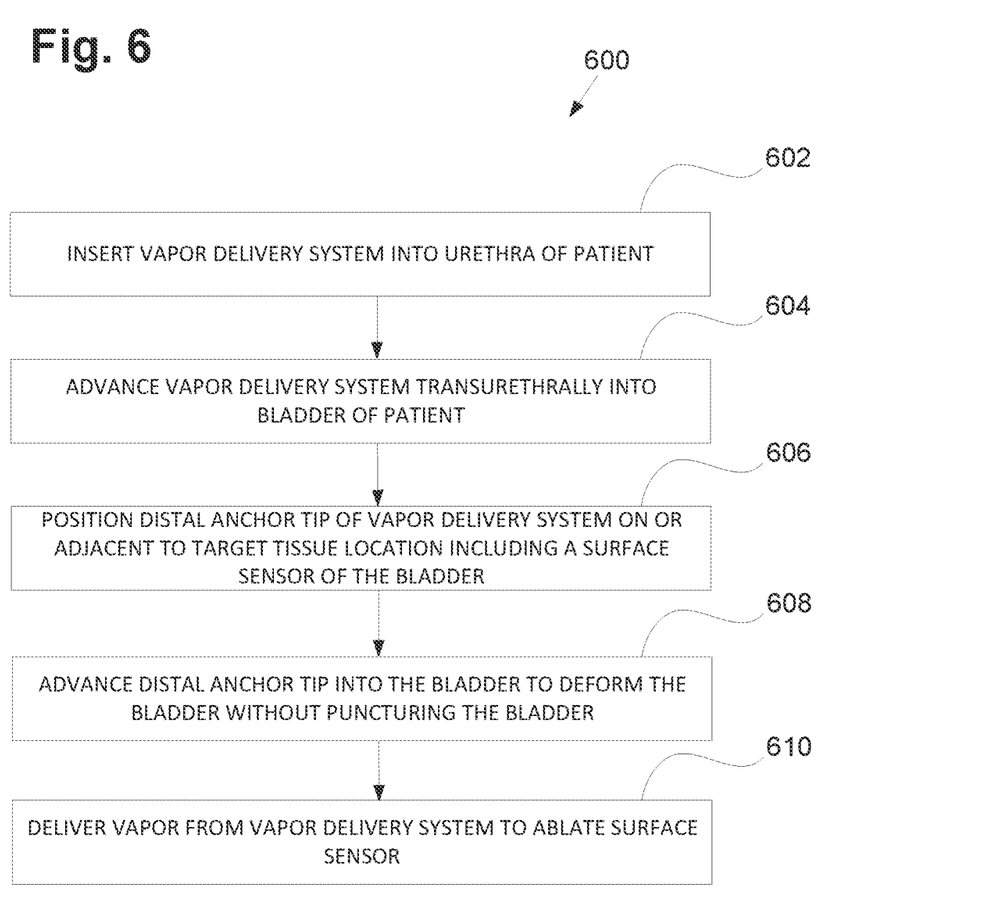
FIG. 6 is a flowchart illustrating a method of treatment using the vapor delivery system.

In FIGS. 5A-5B shows a vapor delivery system 100 and anchor tip 108 inserted into a bladder of a patient. FIG. 5B shows a close-up view of the anchor tip. FIG. 6 shows a flowchart 600 describing a method for treating overactive bladder in a patient, which can comprise the following steps: First, (at step 602 of flowchart 600 in FIG. 6) a shaft including an anchor tip 108 of a vapor delivery system 100, such as the one described above, can be inserted into a urethra of the patient. In some embodiments, the shaft of the vapor delivery system is inserted into a cystoscope which is inserted into the urethra of the patient. In other embodiments, the shaft of the vapor delivery system itself can be inserted into the urethra.

Next, (at step 604 of flowchart 600 in FIG. 6) the vapor delivery system and/or cystoscope can be advanced transurethrally into the patient until a distal portion of the vapor delivery system including the anchor tip and/or cystoscope is positioned within the bladder.

Next, (at step 606 of flowchart 600 in FIG. 6) a distal anchor tip of the vapor delivery system can be advanced and positioned on or adjacent to a target location including a surface sensor of the bladder responsible for creating an urge incontinence sensation. In embodiments when a cystoscope is used, the distal anchor tip of the vapor delivery system can be extended beyond the end of the cystoscope under visualization through the cystoscope.

Next, (at step 608 of flowchart 600 in FIG. 6) the distal anchor tip can be advanced into the bladder tissue on or adjacent to the surface sensor to deform the bladder tissue without puncturing the bladder tissue. In some embodiments, the distal anchor tip is steerable, and can be turned or deformed to accurately anchor the tip on, near, or adjacent to the surface sensor to be treated.

Finally, (at step 610 of flowchart 600 in FIG. 6) vapor can be delivered through the vapor delivery system to the target tissue including a surface sensor to ablate the surface sensor. Sufficient energy can be delivered by the vapor to the surface sensor to ablate the surface sensor without causing injury to the bladder. In some embodiments, the vapor delivery system is configured to deliver between 1-500 calories of energy to the target tissue. This process can be repeated with other surface sensors in the bladder until all the target surface sensors have been treated.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of treatment, comprising:
    inserting a vapor delivery device into a urethra of a patient, wherein the vapor delivery device includes:
        a shaft; and
        a distal tip, wherein the distal tip is narrower than a portion of the shaft proximal of the distal tip, wherein the portion of the shaft proximal of the distal tip defines a plurality of vapor delivery ports, and wherein the distal tip is distal to each of the plurality of vapor delivery ports;
    advancing the distal tip into a bladder of the patient;
    positioning the distal tip on a surface of a tissue of the bladder;
    advancing the distal tip into the tissue to deform the tissue without puncturing through a thickness of the tissue; and
    delivering vapor through the plurality of vapor delivery ports to the tissue to ablate the surface of the tissue.

2. The method of claim 1, wherein the distal tip tapers to a pointed distal end.

3. The method of claim 2, wherein the distal tip has a conical shape.

4. The method of claim 2, wherein the distal tip has a pyramid shape.

5. The method of claim 2, wherein the pointed distal end is a distalmost end of the vapor delivery device.

6. The method of claim 1, further comprising advancing the distal tip less than 10 mm into the tissue.

7. The method of claim 1, further comprising advancing the distal tip less than 5 mm into the tissue.

8. The method of claim 1, further comprising:
    determining a degree to which the tissue is deformed by observing a distance of a visualization feature from a visualization device.

9. The method of claim 1, further comprising:
    determining a desired pattern of vapor deposition; and
    determining whether a degree of deformation of the tissue corresponds to the desired pattern of vapor deposition.

10. A method of treatment, comprising:
    positioning a vapor delivery device, having a portion defining a plurality of vapor delivery ports, within a bladder of a patient such that a distal tip of the vapor delivery device contacts a surface of a tissue of the bladder, wherein the distal tip is narrower than the portion of the vapor delivery device defining the plurality of vapor delivery ports, wherein the portion defining the plurality of vapor delivery ports is a shaft, and wherein the distal tip is distal to each of the plurality of vapor delivery ports;
    advancing the distal tip into the surface of the tissue such that the distal tip deforms the tissue but does not puncture through a thickness of the tissue; and
    delivering vapor through the plurality of vapor delivery ports to the surface of the tissue to ablate the tissue.

11. The method of claim 10, wherein the distal tip tapers to a pointed distal end.

12. The method of claim 11, wherein the pointed distal end is a distalmost end of the vapor delivery device.

13. The method of claim 10, wherein the portion of the vapor delivery device defining the plurality of vapor delivery ports is adjacent to and proximal of the distal tip.

14. The method of claim 10, further comprising:
    determining a desired pattern of vapor deposition;
    determining a degree to which the tissue is deformed by observing a distance of a visualization feature from a visualization device; and
    determining whether the degree to which the tissue is deformed corresponds to the desired pattern of vapor deposition.

15. A method of treatment, comprising:
    determining a thickness of a tissue of a bladder of a patient;
    inserting a vapor delivery device into a urethra of the patient;
    advancing a distal tip of the vapor delivery device into the bladder, wherein the distal tip is narrower than a portion of the vapor delivery device proximal of and adjacent to the distal tip, wherein the portion of the vapor delivery device proximal of and adjacent to the distal tip defines a plurality of vapor delivery ports, wherein the portion of the vapor delivery device proximal of and adjacent to the distal tip is a shaft, and wherein the distal tip is distal tip is distal to each of the plurality of vapor delivery ports;

positioning the distal tip of the vapor delivery device on a surface of the tissue;

advancing the distal tip into the tissue to deform the tissue without puncturing through the thickness of the tissue; and delivering vapor through the plurality of vapor delivery ports to the tissue to ablate the tissue.

16. The method of claim 15, wherein the distal tip tapers to a pointed distal end.

17. The method of claim 16, wherein the pointed distal end is a distalmost end of the vapor delivery device.

18. The method of claim 15, further comprising:

determining a desired pattern of vapor deposition;

determining a degree to which the tissue is deformed by observing a distance of a visualization feature from a visualization device; and determining whether the degree to which the tissue is deformed corresponds to the desired pattern of vapor deposition.

* * * * *